(12) United States Patent
Silver

(10) Patent No.: US 6,974,440 B2
(45) Date of Patent: Dec. 13, 2005

(54) BREASTPUMP WITH COMPLIANT FEATURE

(75) Inventor: Brian H. Silver, Cary, IL (US)

(73) Assignee: Medela Holding AG, Baar (SE)

( * ) Notice: Subject to any disclaimer, the term of this patent is extended or adjusted under 35 U.S.C. 154(b) by 0 days.

(21) Appl. No.: 10/116,190

(22) Filed: Apr. 4, 2002

(65) Prior Publication Data

US 2003/0191432 A1 Oct. 9, 2003

(51) Int. Cl.[7] .......................... A61M 1/26; A61M 1/06; A41D 13/08; A61J 3/00; A61J 9/00

(52) U.S. Cl. ...................... 604/74; 604/75; 604/76; 2/20; 215/11.1; 119/14.01

(58) Field of Search ................ 604/320, 74–78, 604/315, 346, 34, 115, 132, 250, 85, 518, 507, 153, 131; 417/415; 251/208; 601/14; 422/101; 119/14.02, 14.01; 215/11.1–11.6; 2/20

(56) References Cited

U.S. PATENT DOCUMENTS

| | | | |
|---|---|---|---|
| 4,583,970 A | * | 4/1986 | Kirchner ....................... 604/74 |
| 4,929,229 A | | 5/1990 | Larsson |
| 5,007,899 A | | 4/1991 | Larsson |
| 5,358,476 A | * | 10/1994 | Wilson ......................... 604/74 |
| 5,746,850 A | * | 5/1998 | Luscher et al. ........... 152/339.1 |
| 5,806,091 A | * | 9/1998 | McHugh ........................... 2/20 |
| 6,073,788 A | * | 6/2000 | Stroud ........................ 215/11.1 |
| 6,110,140 A | | 8/2000 | Silver |
| 6,152,896 A | * | 11/2000 | Bachman et al. .............. 604/74 |
| 2004/0024351 A1 | * | 2/2004 | Greter et al. .................. 604/74 |

* cited by examiner

*Primary Examiner*—Nicholas D. Lucchesi
*Assistant Examiner*—Roz Maiorino
(74) *Attorney, Agent, or Firm*—Baniak Pine & Gannon

(57) ABSTRACT

A breastpump assembly includes a hood member having a funnel-shaped shield portion for placement over a breast and a sleeve portion extending from the funnel-shaped portion. The breastpump assembly includes a substantially rigid plastic housing connected to the extending portion of the breast hood. A pump is fixed or functionally attached to the housing for applying a negative pressure to the housing. A container is attached to the housing, the container being in fluid communication with the breast hood to receive expressed breast milk. At least a portion of the breastpump exterior surface includes a compliant portion.

12 Claims, 2 Drawing Sheets

BREASTPUMP WITH COMPLIANT FEATURE

TECHNICAL FIELD

The present invention relates to breastmilk pumps, and particularly relates to a breastpump that includes elements having a compliant material placed on the pump.

BACKGROUND OF THE INVENTION

Pumps used to extract or express milk are well known. Breastmilk pumps are adapted to apply a vacuum to the breast in order to express it of its contents of milk, such as for storage in a container for later use by an infant.

Breastmilk pumps generally include a breastshield (also known as a hood) that typically includes a funnel-shaped surface sized and shaped to fit over the breast; a vacuum source connected to the breastshield for generating an intermittent reduced pressure, i.e., a vacuum, within the breastshield; and, a housed conduit structure for communicating milk from the breastshield to a container for the expressed milk, as well as for communicating pressure variations (such as the foregoing vacuum) to the breastshield. An example of this type of pump is shown in U.S. Pat. No. 5,007,899. Some breastpumps are designed to be operated with either one hand or two hands by using a lever. An example of this type of pump is shown in U.S. Pat. No. 6,110,140. As a result of the pressure changes produced and transferred therethrough and other reasons, the housing, conduit and breastshield portions of the breastpump tend to be made of a relatively rigid material.

When pumping a breast manually, it may take a considerable amount of time to empty. The rigid material of the pump may contribute to problems related to lack of grip and discomfort. In addition, the repetitiveness of the pumping motion can lead to user fatigue and discomfort. As a result, the user may use the breastpump for short periods only, may stop using the breastpump altogether or may turn to electric pumps instead of manual pumps.

Also, the operation of some types of breastpumps can cause various parts of the breastpump to come into sudden or abrupt contact with each other. This contact between parts may create undesired noise or vibrations to occur, which may disrupt the process of pumping and extracting breastmilk.

A demand therefore exists for an improved breastpump that reduces or eliminates the problems of discomfort, fatigue, frustration, and noise and is more desirable to the consumer.

SUMMARY OF THE INVENTION

An objective of the present invention is to alleviate the drawbacks described above by improving the feel and handling of a breastpump with an ergonomically designed compliant feature. The compliant feature can provide a manual breastpump with increased grip while holding and operating the pump and is more comfortable to hold and operate. The compliant feature may provide a reduction of noise and vibration when various parts of the breastpump come into contact with each other. The compliant feature may provide a pleasant appearing surface or feature as opposed to or in concert with the smooth and hard plastic substrate upon which it is positioned. The compliant feature may provide a surface upon which indicia may be more easily applied or viewed compared to the plastic substrate making up the main elements of the breastpump.

One aspect of the present invention provides a breastpump assembly including a hood member. The hood member includes a funnel-shaped shield portion for placement over a breast and a sleeve portion extending from the shield portion. The hood member includes a first exterior surface. A substantially rigid housing is connected to the sleeve, the rigid housing includes a second exterior surface. A mechanism for applying a negative pressure to the rigid housing is provided. The mechanism includes a third exterior surface. At least a portion of the breastpump assembly includes a compliant material positioned on at least a portion of at least one of the exterior surfaces.

A further aspect of the present invention provides a container attached to the rigid housing. The container is in fluid communication with the breast hood for receiving expressed breast milk and includes a fourth exterior surface. The breastpump assembly may include compliant material positioned on at least a portion of the fourth exterior surface. The compliant material may be positioned on at least a portion of the shield portion of the first exterior surface. The compliant material may be positioned on at least a portion of the sleeve portion of the first exterior surface. The means for applying a negative pressure may include a pump. The pump may include a handle. The handle may include a fifth exterior surface. The compliant material may be positioned on at least a portion of the fifth exterior surface. The compliant material may be positioned on at least a portion of the second exterior surface. The compliant material may be positioned on the entire area of the exterior surfaces.

Yet another aspect of the present invention provides a breastpump assembly wherein the compliant material held by a hand yields under pressure from the hand for increased comfort and grip of the compliant area. The compliant material includes a tactile, compliant material arranged along at least one of the exterior surfaces of the breastpump assembly normally used for gripping by a user. The compliant material is resiliently compressible so that the user fingers may deform the compliant material to provide additional traction during use, the compliant material being formed from a soft, resiliently deformable, generally anti-slip material. The compliant material can be fabricated of one or more elastomeric material. The compliant material can be fabricated of one or more of a thermoset and a thermoplastic elastomer. The thermoset elastomer may include one or more of a natural rubber, a butyl rubber, a nitrile rubber, a chloroprene rubber, a silicone rubber and an acrylic rubber. The thermoplastic elastomer may include one or more of a styrene-butadiene-styrene based material, a polyolefin based material, a nylon or nylon copolymer material, a chlorinated polyethylene based material and polyester based elastomeric material. The compliant material may be provided in the form of a layer of elastomeric material, a plurality of elastomeric ribs or in the form of one or more layer, strip, dot, crosshatch, bar, ridge, tip and pad or the like.

Yet another aspect of the present invention provides a breastpump assembly including a hood member for placement over a breast. The hood member has a funnel-shaped shield portion within which the breast is received. A manual pump is operatively connected with the hood member. The pump may further include a cylinder and a piston slidably engaged with the cylinder for reciprocating movement occurring along an axis, whereby the reciprocating movement generates an alternating pressure in the hood member on the breast to express milk therefrom. A piston rod is connected to the piston, the piston rod including an extension member where a first hand is placed. A container for expressed milk is connected to the assembly in communication with the funnel shaped portion, the container being located downstream from the funnel-shaped portion. A tactile compliant material is provided on at least a part of a compliant area which is held by a second hand, the tactile compliant material being resiliently compressible and yielding under pressure from the hand for increased comfort and grip of the compliant area.

In yet another aspect of the invention, the breastpump assembly includes a housing including a hood member. A pump is attached to the housing. The pump may be a diaphragm pump including a handle member operatively connected to a diaphragm. The diaphragm defines a vacuum chamber with the housing. Movement of the handle member displaces the diaphragm and generates a negative pressure in the vacuum chamber. Such negative pressure is applied to a breast positioned in the hood member. A tactile compliant material is provided to one or more surfaces of the housing, hood member and pump handle.

The objectives, advantages and features of the invention will be further appreciated upon consideration of the following detailed description of an embodiment taken in conjunction with the drawings.

DETAILED DESCRIPTION OF EMBODIMENTS OF THE INVENTION

Figure 1:
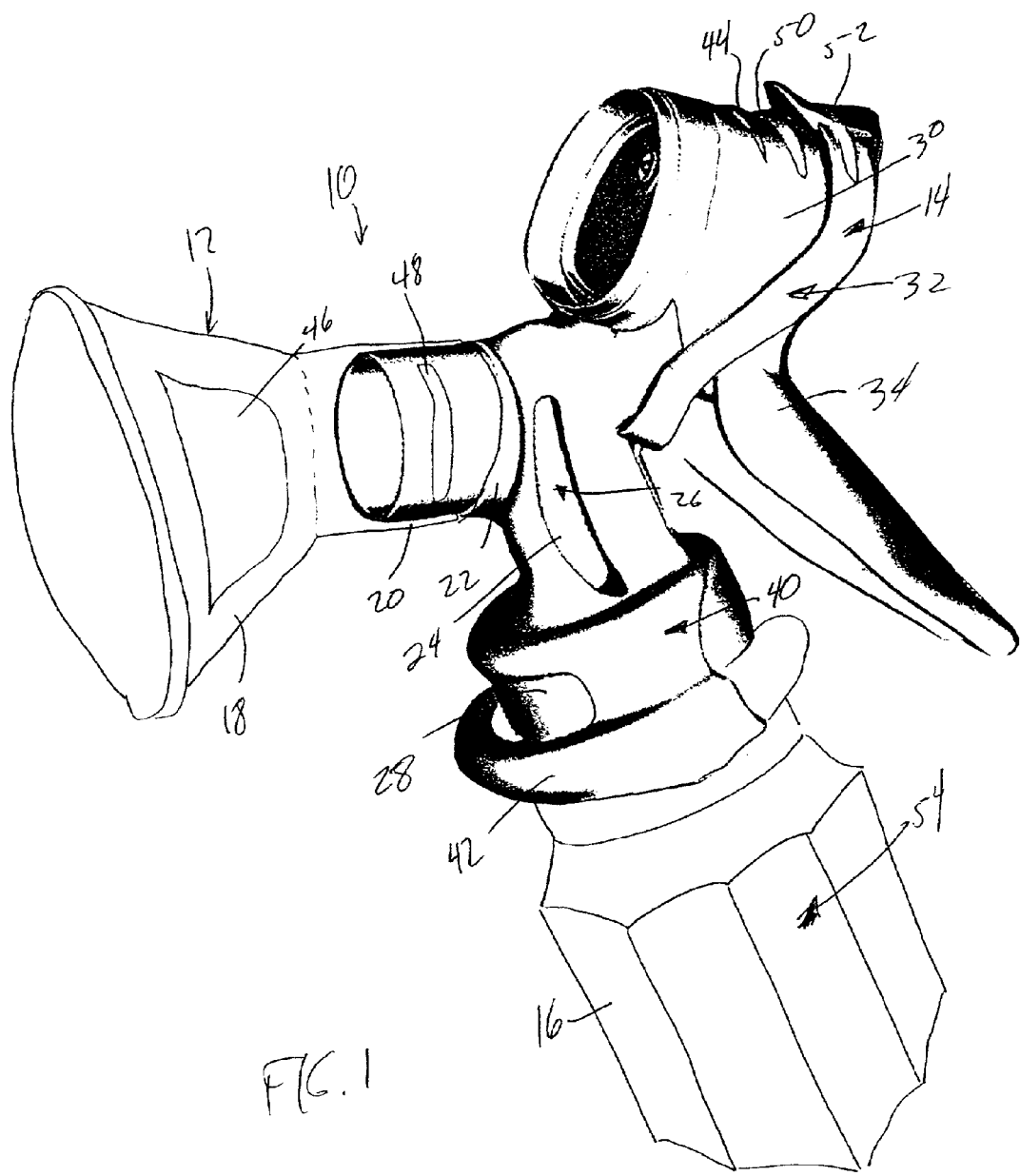
FIG. 1 is a perspective view of a manual breastpump according to the present invention.

As shown in FIG. 1, and in broad overview, an embodiment of the breastpump assembly 10 according to the present invention comprises a housing 24, with a hood member 12, a pump member 14 and a container 16, each of which is attachable to or formed integrally with the housing. The housing 24 generally includes sleeve mount 22, collection chamber 26, container mount 28 and pump mount 30. The hood member 12 includes a funnel-shaped shield end 18 and an integral tubular sleeve end 20 opposite the funnel-shaped shield end. Integral tubular sleeve end 20 may attach to sleeve mount 22 of the housing 24, for example, in an interference fit. For purposes of the present invention, the shape of the hood assembly and its connection to the housing 24 of the breastpump assembly 10 are incidental; the particular arrangement and details of these elements is in no way limiting. In one embodiment, the hood member 12 and housing 24 including the container mount 28 and pump mount 30 are formed integrally or, in other words, formed as a one-piece unit. It will be understood that, in the alternate, separate, connectable members may used to construct the breastpump assembly 10.

The breastpump assembly illustrated herein may include a manually or otherwise operated breastpump, which is shown set up for manual operation in FIG. 1. The breastpump assembly 10 may include a hand-driven pump 32, for example, a diaphragm pump, activated by a handle 34, which operates in a manner that will be described in more detail hereafter. The pump 32 may be releasably attached to the housing portion 24 at a back portion thereof, or in a pump housing 30 portion of the housing 24 opposite the hood assembly 12. Generally, the pump 32 may include an outer cylindrical portion and a diaphragm (not shown) positioned within the outer cylindrical portion. A handle 34, which may be in the form of a lever, extension or the like, may be provided for manual or motor activation of the pump. Details of breastpump functioning can be further gleaned from U.S. Pat. Nos. 6,110,140; 5,007,899 and 4,929,229. In the alternate, the breastpump assembly 10 may also be operated by a motor drive unit, (not shown), as is known in the art, either with or without pump 32.

Breastpump assembly 10 is made of a rigid material, such as, for example, polypropylene or polycarbonate plastic. The rigid material of the pump assembly 10 can be used to make up the housing 24, hood assembly 12, pump member 14, container 16, mounts 22, 28 and 30. It will be understood that the exterior of the rigid material provides an exterior surface on all elements made therefrom having a texture and composition for receiving a compliant material, generally indicated at 40. The compliant material 40 may be provided to some or all of the exterior surfaces of the breastpump assembly 10. It may be provided in a thickness of about 0.3 mm to 10 mm. The compliant material may be provided as a continuous piece as indicated at 42 on housing 24 or as ribs 44 on pump housing 30 or other compliant patterns, such as, for example, dots, checks, cross-hatch, and straight or curved lines, and so on. In other embodiments, the compliant material 40 may be positioned on all or any of the outer surfaces of the hood member 12 at 46 and 48. It may be advantageous to position compliant material 40 on exterior surfaces 50, 52 of the pump housing 30 and handle 34 as well as exterior surfaces 54 of the container 16. Further, as shown in FIG. 1, compliant material 40 may be provided to the housing 24.

While there are advantages directed to providing a number of optional compliant alternatives to the breastpump assembly 10 by coating most or the entire breastpump, it may also be beneficial to coat only selected portions thereof. For example, if only a portion of the breastpump assembly 10 is provided with a compliant material, viewing the contents or fullness of the container and discerning the cleanliness of the interior of the housing may be made possible, for example. Therefore, in the alternate, the invention includes providing compliant surfaces to the breastpump assembly 10 by applying compliant material 40, for example, on the housing 24 as shown in FIG. 1.

Thus, alternate embodiments of the present invention contemplate the outer surface of the breastpump assembly 10 being completely or partially covered with a soft material for providing better grip and less stress on the hands, for example. Elastomeric, polymeric and rubber materials are generic examples of types of material for this soft outer layer.

The compliant material 40 may be made of any suitable soft resilient, compliant or tactile material being compressible to some degree relative to the substrate from which the breastpump is constructed. The compliant material 40 may be formed of a natural or synthetic elastomeric or polymeric material, or any other suitable material that exhibits, for example, enhanced compliant, grip or tactile properties. The elastomeric materials may include thermoset and thermoplastic elastomers and thermoplastic polymeric rubbers. The thermoset elastomer may be selected from the class of thermoset elastomers including natural rubber, butyl rubber, nitrile rubber, chloroprene, silicone rubber and acrylic rubber. The thermoplastic rubber may be selected from a class of thermoplastic rubbers including, but not limited to: styrene-butadiene-styrene (SBS) and like families of diblock and triblock thermoplastic elastomers, thermoplastic polyolefins (TPO's) composed of polypropylene continuous phase with dispersed rubber phase of neoprene, chlorinated polyethylene, and other crossed linked rubber dispersed phase, polyester thermoplastic elastomers, thermoplastic polyurethane (TPU), nylon and nylon copolymer materials and blends thereof. Examples of preferred compliant materials 40 include Santoprene® (a thermoplastic rubber available from Advanced Elastomer Systems) Kraton® and Dynaflex® (available from GLS Corporation) and C-FLEX® (available from Consolidated Polymer Technologies, Inc.). It will be understood that alternate materials having beneficial compliant properties are also contemplated by the present invention.

In another embodiment of the present invention, the compliant material 40 is confined to ergonomic gripping positions on the breastpump assembly, which will be explained more fully below. In this embodiment, the tactile compliant material is placed so as to lessen the likelihood of user fatigue with respect to gripping and therefore improve the ergonomics of the pump assembly 10.

Examples of preferred areas to which an amount of compliant material may be applied include, for example, the shield end 18, the integral tubular sleeve end 20, the housing 24, the pump mount 30, and handle 34. It will be understood that variations of the compliant areas may be made according to how the user holds the breastpump assembly 10 and that ergonomic placement of compliant material 40 would preferably coincide with one or more of the areas that are gripped or contacted by a user. Compliant material 40 may be placed on the breastpump assembly 10 to allow several holding variations on the same pump.

The compliant material 40 may be provided to the pump assembly 10 according to a variety of methods. For example, the compliant material 40 may be molded or applied to the pump assembly 10 during the molding process. One type of molding process that may be used for this purpose is "double shot" molding where a rigid plastic portion is molded first (the rigid plastic housing 24, for example) and then the soft compliant material is molded upon the rigid plastic in a single machine designed for such a process. In another example, the process may include "over molding", using two or more molds, each of the molds designed for injection of the materials in subsequent steps including a rigid plastic molding step and the application of a soft compliant material thereto. The compliant material 40 may be mechanically slipped or shrunk onto the pump assembly 10. The compliant material 40 may be glued to the pump assembly 10 or fitted thereto by any suitable process.

A container 16 for the collection of breast milk, such as a bottle or other suitable type of receptacle may be releasably attached to the container mount 28 of the breast-hood housing 24. The pump 32 and container 16 may be releasably connected to the housing 24, for example, by threaded engagement with the housing or any other suitable means.

As to the manner of usage and operation of the present invention, the same should be apparent from the above description. It is to be realized, then, that the optimum dimensional variations in size, materials, shape, form, function and manner of operation, assembly, application and use, are deemed readily apparent to one skilled in the art, and all equivalent relationships to those illustrated in the drawings and described in the specification are intended to be encompassed by the present invention.

Figure 2:
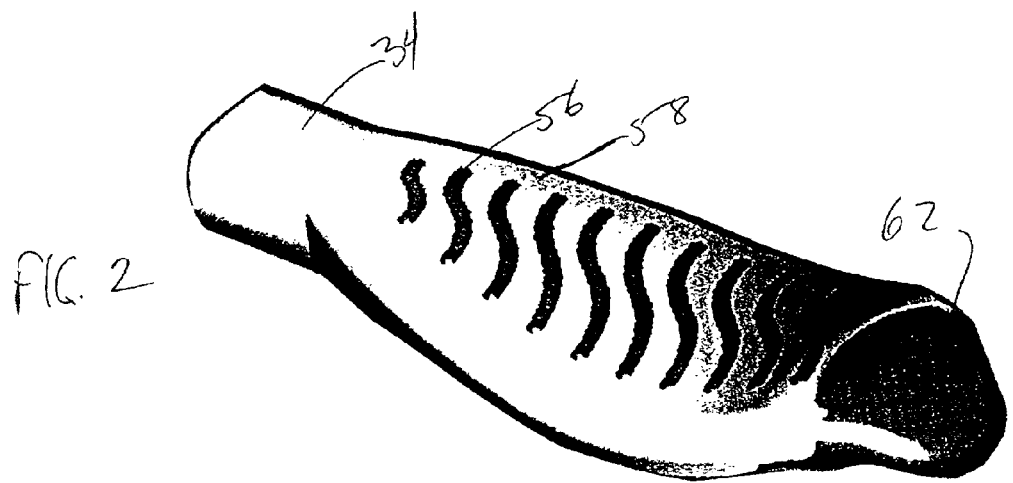
FIG. 2 is a top perspective view of a handle for a manual breastpump according to the present invention.

FIG. 2 shows an embodiment of the present invention including pump handle 34 having a top surface 58 including a plurality of curved compliant ribs 56 made of the compliant material 40 and distributed along the length of the top surface 58 of the handle 34. Some or all of the ribs 56 may be oriented generally transversely to the long axis of the handle 34. The ribs 56 may be straight, arcuate or S-shaped as shown. Other rib shapes may be utilized as desired. Further, the handle 34 includes a free end 60 having a coated compliant tip 62.

Figure 3:
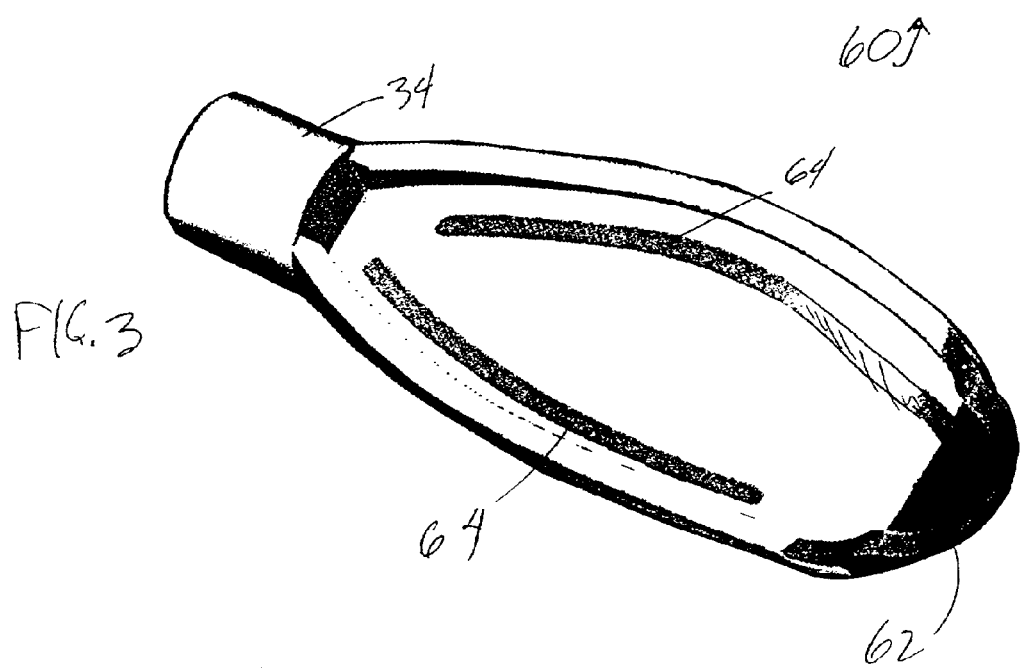
FIG. 3 is a bottom perspective view of a handle for a manual breastpump according to the present invention.
Figure 1:
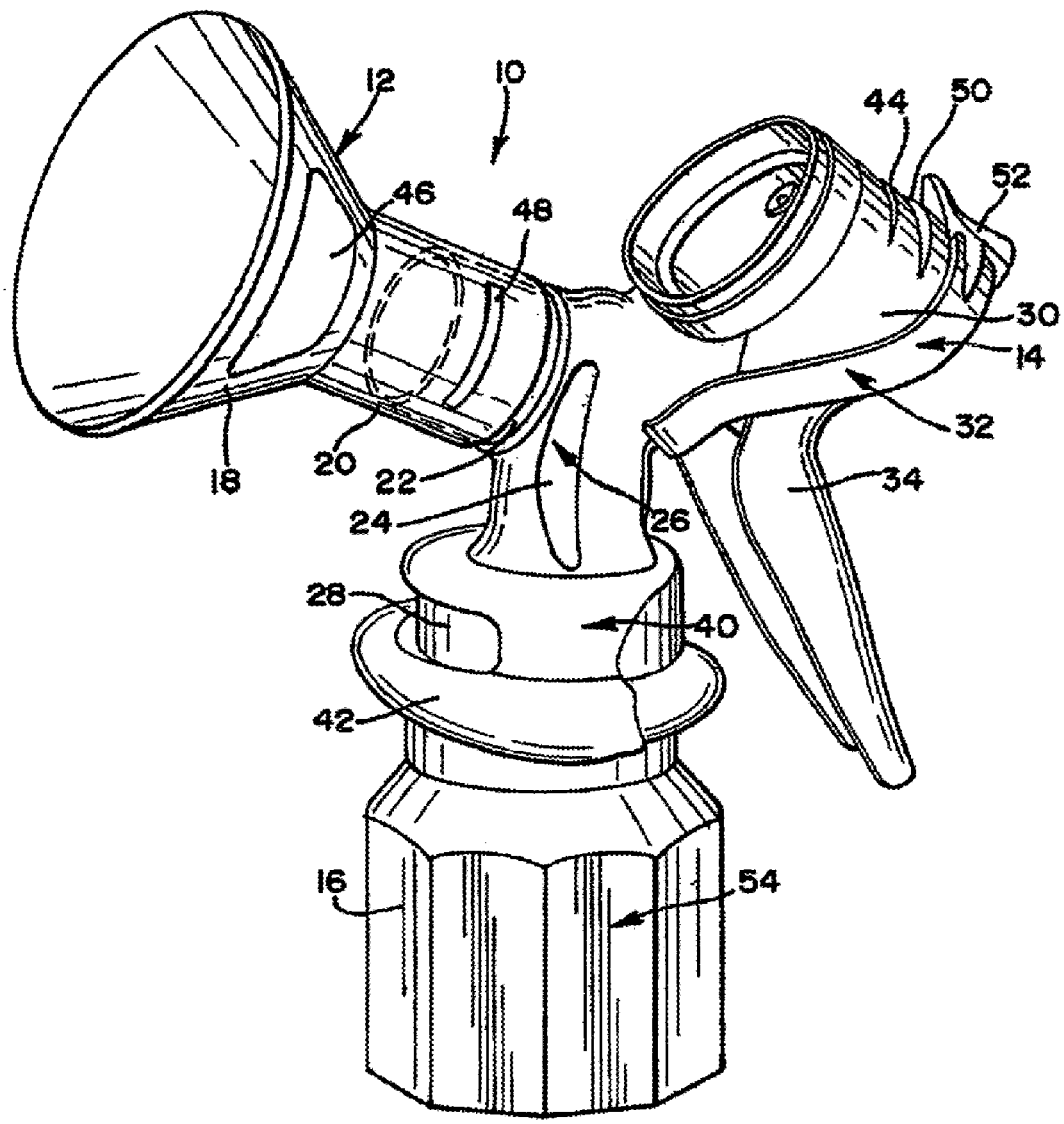
Figure 2:
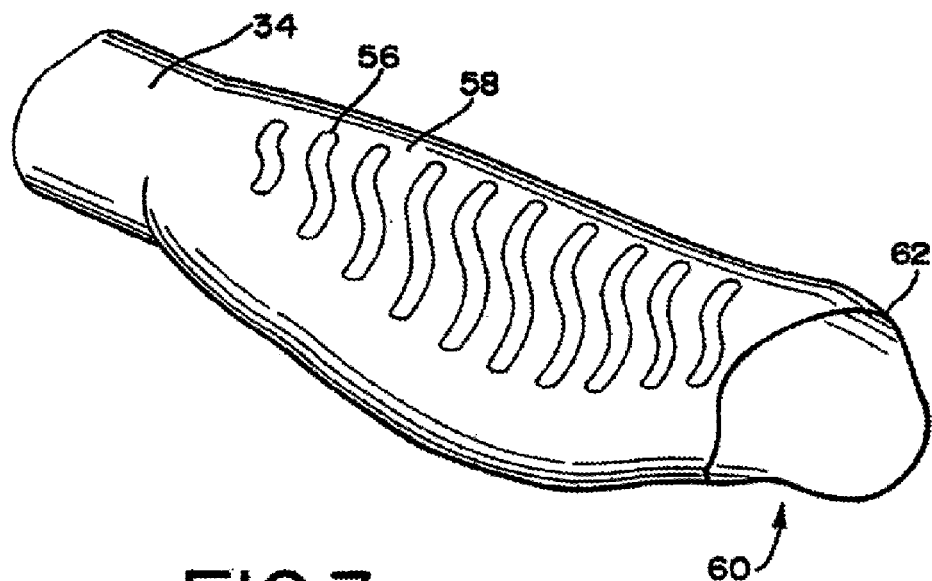
Figure 3:
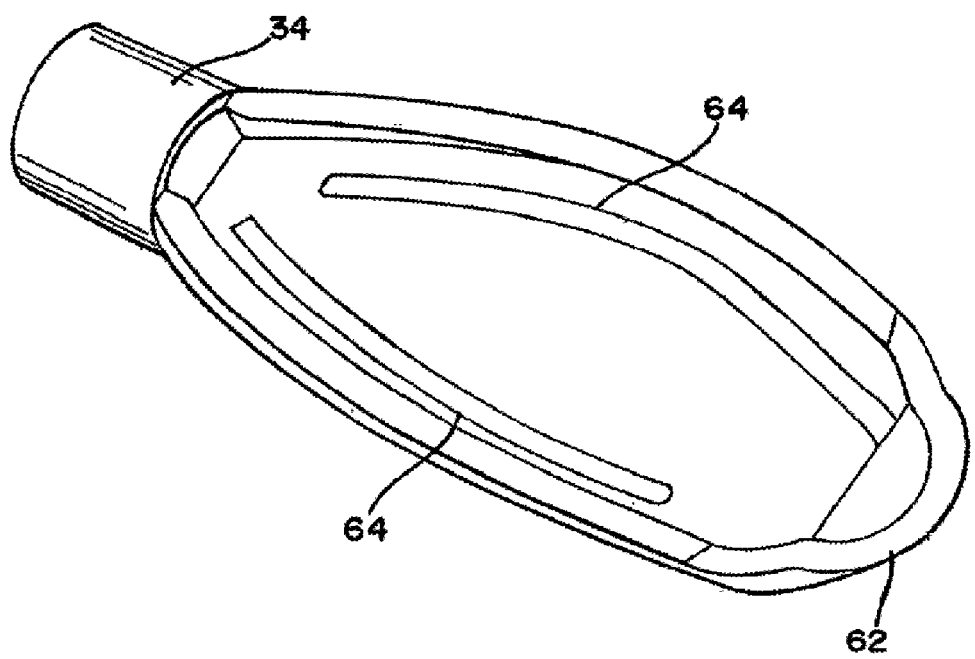

FIG. 3 shows an embodiment of the present invention wherein the pump handle 34 includes an underside that may include one or more compliant portions 64. The compliant portions 64 may be in the form of a plurality of strips or the like, preferably arranged in a longitudinal orientation along the handle 34, for example, by fastening the strips onto or imbedding within the handle.

While particular embodiments of the present invention are disclosed herein, it will be understood that such embodiments are examples of an invention that may encompass various and alternative forms. Therefore, the specific structural and functional details disclosed herein are not intended to be limiting, but merely exemplify the literal and equivalent scope of the invention as claimed below.

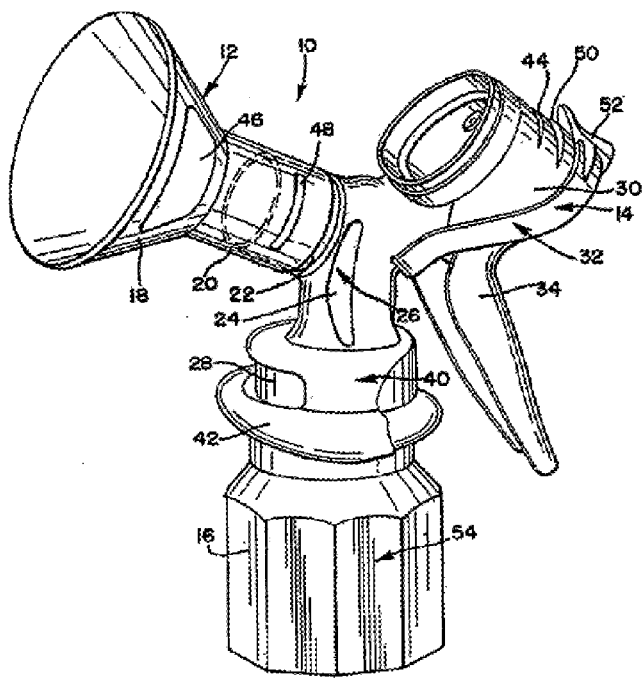

What is claimed is:

1. A breastpump assembly comprising:
   a rigid material;
   a compliant material being resiliently compressible relative to said rigid material by a user's hand in use of the breastpump assembly;
   a hood member made of said rigid material, said hood member including a funnel-shaped shield portion for placement over a breast and a sleeve portion extending from said funnel-shaped shield portion;
   a housing made of said rigid material connected to said sleeve portion;
   a movable handle made from said rigid material sized and shaped to be grasped by the hand for applying a negative pressure to said housing when manipulated; and
   said compliant material being positioned on said rigid material on at least a portion of said movable handle to facilitate and ease repeated grasping of said movable handle by the user's hand and thereby ergonomically improve the breastpump assembly.

2. The breastpump assembly of claim 1 further comprising a container made of said rigid material, said container releasably attached to said housing and in fluid communication with said hood member for receiving expressed breast milk.

3. The breastpump assembly of claim 1 wherein said compliant material is resiliently compressible so that fingers of a user may deform said compliant material to provide additional grip during use, said compliant material being formed from a soft, resiliently deformable, generally anti-slip material.

4. The breastpump assembly of claim 1 wherein said compliant material is provided in the form of a plurality of elastomeric ribs.

5. The breastpump assembly of claim 4 wherein said ribs are orientated transversely to the long axis of said handle.

6. The breastpump assembly of claim 4 wherein said ribs are one or more of straight, arcuate and S-shaped.

7. The breastpump assembly of claim 4 wherein said ribs are distributed along a length of a top surface of said handle.

8. The breastpump assembly of claim 1 wherein said movable handle includes an underside that includes compliant material.

9. The breastpump assembly of claim 1 wherein said compliant material is provided in the form of one or more layer, strip, dot, crosshatch, bar, ridge, tip and pad.

10. The breastpump assembly of claim 1 wherein said compliant material is provided with printed indicia.

11. The breastpump assembly of claim 1 wherein said compliant material is positioned on at least a portion of said hood member.

12. The breastpump assembly of claim 11 wherein said compliant material is positioned on at least a portion of said housing.

* * * * *

UNITED STATES PATENT AND TRADEMARK OFFICE
CERTIFICATE OF CORRECTION

PATENT NO. : 6,974,440 B2  Page 1 of 4
APPLICATION NO. : 10/116190
DATED : December 13, 2005
INVENTOR(S) : Brian H. Silver It is certified that error appears in the above-identified patent and that said Letters Patent is hereby corrected as shown below:

In the Title Page replace Print Fig 1, and in the Drawings, "informal Figs. 1-3" are replaced with --formal Figs. 1-3--. see attached Signed and Sealed this Seventh Day of November, 2006

JON W. DUDAS
*Director of the United States Patent and Trademark Office*

(12) United States Patent
Silver

(10) Patent No.: US 6,974,440 B2
(45) Date of Patent: Dec. 13, 2005

(54) BREASTPUMP WITH COMPLIANT FEATURE

(75) Inventor: Brian H. Silver, Cary, IL (US)

(73) Assignee: Medela Holding AG, Baar (SE)

(*) Notice: Subject to any disclaimer, the term of this patent is extended or adjusted under 35 U.S.C. 154(b) by 0 days.

(21) Appl. No.: 10/116,190

(22) Filed: Apr. 4, 2002

(65) Prior Publication Data
US 2003/0191432 A1 Oct. 9, 2003

(51) Int. Cl.[7] .................. A61M 1/26; A61M 1/06; A41D 13/08; A61J 3/00; A61J 9/00
(52) U.S. Cl. .................. 604/74; 604/75; 604/76; 2/20; 215/11.1; 119/14.01
(58) Field of Search .................. 604/320, 74–78, 604/315, 346, 34, 115, 132, 250, 85, 518, 507, 153, 131; 417/415; 251/208; 601/14; 422/101; 119/14.02, 14.01; 215/11.1–11.6; 2/20

(56) References Cited

U.S. PATENT DOCUMENTS

| | | | |
|---|---|---|---|
| 4,583,970 A | * 4/1986 | Kirchner | 604/74 |
| 4,929,229 A | 5/1990 | Larsson | |
| 5,007,899 A | 4/1991 | Larsson | |
| 5,358,476 A | * 10/1994 | Wilson | 604/74 |
| 5,746,850 A | * 5/1998 | Luscher et al. | 152/339.1 |
| 5,806,091 A | * 9/1998 | McHugh | 2/20 |
| 6,073,788 A | * 6/2000 | Stroud | 215/11.1 |
| 6,110,140 A | 8/2000 | Silver | |
| 6,152,896 A | * 11/2000 | Bachman et al. | 604/74 |
| 2004/0024351 A1 | * 2/2004 | Greter et al. | 604/74 |

* cited by examiner

Primary Examiner—Nicholas D. Lucchesi
Assistant Examiner—Roz Maiorino
(74) Attorney, Agent, or Firm—Baniak Pine & Gannon

(57) ABSTRACT

A breastpump assembly includes a hood member having a funnel-shaped shield portion for placement over a breast and a sleeve portion extending from the funnel-shaped portion. The breastpump assembly includes a substantially rigid plastic housing connected to the extending portion of the breast hood. A pump is fixed or functionally attached to the housing for applying a negative pressure to the housing. A container is attached to the housing, the container being in fluid communication with the breast hood to receive expressed breast milk. At least a portion of the breastpump exterior surface includes a compliant portion.

12 Claims, 2 Drawing Sheets